United States Patent
Wang et al.

(10) Patent No.: US 12,036,424 B2
(45) Date of Patent: Jul. 16, 2024

(54) RADIATION THERAPY HEAD AND RADIATION THERAPY APPARATUS

(71) Applicants: OUR UNITED CORPORATION, Xi'an (CN); SHENZHEN OUR NEW MEDICAL TECHNOLOGIES DEVELOPMENT CO., LTD., Shenzhen (CN)

(72) Inventors: Huiliang Wang, Xi'an (CN); Ming Zhong, Xi'an (CN); Hongbin Zhao, Xi'an (CN)

(73) Assignees: Our United Corporation, Xi'an (CN); Shenzhen Our New Medial Technologies Development Co., Ltd., Shenzhen (CN)

( * ) Notice: Subject to any disclaimer, the term of this patent is extended or adjusted under 35 U.S.C. 154(b) by 932 days.

(21) Appl. No.: 17/051,369

(22) PCT Filed: Apr. 8, 2019

(86) PCT No.: PCT/CN2019/081784
§ 371 (c)(1),
(2) Date: Oct. 28, 2020

(87) PCT Pub. No.: WO2019/205924
PCT Pub. Date: Oct. 31, 2019

(65) Prior Publication Data
US 2021/0093892 A1    Apr. 1, 2021

(30) Foreign Application Priority Data
Apr. 28, 2018  (CN) ......................... 201810405002.7

(51) Int. Cl.
| | |
|---|---|
| *A61N 5/00* | (2006.01) |
| *A61N 5/10* | (2006.01) |
| *H01J 35/06* | (2006.01) |
| *H01J 35/08* | (2006.01) |
| *H01J 35/14* | (2006.01) |

(52) U.S. Cl.
CPC ......... *A61N 5/1042* (2013.01); *A61N 5/1081* (2013.01); *H01J 35/064* (2019.05);
(Continued)

(58) Field of Classification Search
None
See application file for complete search history.

(56) References Cited

U.S. PATENT DOCUMENTS 4,827,491 A * 5/1989 Barish .................. A61N 5/1084
378/65
5,267,294 A * 11/1993 Kuroda ................ A61N 5/1084
378/65
5,548,627 A    8/1996 Swerdloff et al.

FOREIGN PATENT DOCUMENTS

| CN | 1107374 A | 8/1995 |
| CN | 1114230 A | 1/1996 |

(Continued)

OTHER PUBLICATIONS

Notification to Grant Patent Right for Invention of Chinese Patent Application No. 201810405002.7—6 pages (Jan. 26, 2021).
(Continued)

*Primary Examiner* — Hoon K Song
(74) *Attorney, Agent, or Firm* — Knobbe, Martens, Olson & Bear, LLP

(57) ABSTRACT

A radiotherapy head can include an electron accelerator, a deflection control assembly, a collimator, and a target material. The deflection control assembly is provided between the electron accelerator and the collimator, the collimator is provided with a plurality of collimating holes, and the target material is provided at an entrance of the each of the plurality of collimating holes; the deflection control assembly is configured to adjust a deflection angle of electron beams emitted by the electron accelerator, and emit angle-deflected electron beams to the target material; the target (Continued)

material is configured to convert the electron beams emitted to the target material into X-rays; and the collimator is configured to project the X-rays to a target via the plurality of collimating holes.

12 Claims, 2 Drawing Sheets

(52) U.S. Cl.
CPC .............. *H01J 35/08* (2013.01); *H01J 35/14* (2013.01); *A61N 2005/1091* (2013.01); *A61N 2005/1095* (2013.01)

(56) References Cited

FOREIGN PATENT DOCUMENTS

| | | |
|---|---|---|
| CN | 1185981 A | 7/1998 |
| CN | 1666301 A | 9/2005 |
| CN | 1676177 A | 10/2005 |
| CN | 2870897 Y | 2/2007 |
| CN | 105326519 A | 2/2016 |
| CN | 105470077 A | 4/2016 |
| CN | 105636331 A | 6/2016 |
| CN | 108478941 A | 9/2018 |
| CN | 208756809 U | 4/2019 |
| EP | 0747094 A2 | 12/1996 |
| WO | 2017177405 A1 | 10/2017 |

OTHER PUBLICATIONS

International Search Report and Written Opinion of PCT Application PCT/CN2019/081784—20 pages(Jun. 27, 2019).
First Office Action of Chinese Application No. 201810405002.7—14 pages (Jul. 22, 2019).
Second Office Action of Chinese Application No. 201810405002.7—13 pages (Mar. 20, 2020).
Third Office Action of Chinese Application No. 201810405002.7—16 pages (Jul. 2, 2020).

* cited by examiner

RADIATION THERAPY HEAD AND RADIATION THERAPY APPARATUS

CROSS-REFERENCE TO RELATED APPLICATION

The present disclosure is the national phase of International Application No. PCT/CN2019/081784, titled "RADIATION THERAPY HEAD AND RADIATION THERAPY APPARATUS", filed on Apr. 8, 2019, which claims priority to Chinese Patent Application No. 201810405002.7, filed on Apr. 28, 2018 and titled "RADIOTHERAPY APPARATUS", the contents of which are incorporated herein by reference in their entireties.

TECHNICAL FIELD

The present disclosure relates to the field of medical technologies and in particular, relates to a radiotherapy head and a radiotherapy apparatus.

BACKGROUND

In modern medicine, radiotherapy is an important means of treating tumors. A radiotherapy device for radiotherapy includes a gantry and a radiotherapy head. The radiotherapy head is provided on the gantry, a center of the gantry is provided with an opening for accommodating a treatment couch. The radiotherapy head generally includes a radiation source and a collimator. Rays emitted by the radiation source are shaped by the collimator and then irradiated to a tumor focus region, thereby killing tumor cells in the tumor focus region.

Current focused radiotherapy technologies include a gamma knife technology using a cobalt-60 (Co60) radiation sources and an X-ray knife technology using an electron accelerator. Due to the natural radioactivity of the Co60 radiation source, the problems resulting from radiation protection during its installation, transportation and replacement and from its activity decay over time have always affected the development of the gamma knife technology. Compared with the gamma knife technology, the X-ray knife technology uses the electron accelerator as the radiation source, and the electron accelerator does not lead to any radiation once powered-off. Therefore, the current research and application of the ray knife technology have become increasingly extensive.

SUMMARY

The present disclosure provides a radiotherapy head and a radiotherapy apparatus. The technical solutions are as follows.

In one aspect, a radiotherapy head is provided. The radiotherapy head includes: an electron accelerator, a deflection control assembly, a collimator, and a target material, wherein the deflection control assembly is provided between the electron accelerator and the collimator, the collimator is provided with a plurality of collimating holes, and the target material is provided at an entrance of each of the plurality of collimating holes;

the deflection control assembly is configured to adjust a deflection angle of electron beams emitted by the electron accelerator, and emit angle-deflected electron beams to the target material;

the target material is configured to convert the electron beams emitted to the target material into X-rays; and the collimator is configured to project the X-rays to a target via the plurality of collimating holes.

Optionally, the collimator includes at least one collimating hole set, and each collimating hole set includes a plurality of collimating holes; and the deflection control assembly is configured to adjust the deflection angle of the electron beams emitted by the electron accelerator, the electron beams are made to sequentially impact the target materials at the entrances of the plurality of collimating holes in a target collimating hole set, and the target collimating hole set is one of the at least one collimating hole set.

Optionally, bore diameters of the collimating holes in each collimating hole set are same.

Optionally, the collimator includes a plurality of the collimating hole sets, and bore diameters of the collimating holes in different collimating hole sets are different.

Optionally, bore diameters of the collimating holes in each collimating hole set of the collimator include at least one of 5 mm, 8 mm, 15 mm, 20 mm and 35 mm.

Optionally, the collimator is an arc-shaped focusing collimator.

Optionally, the deflection control assembly includes: oppositely arranged electromagnets; and the oppositely arranged electromagnets are configured to form a deflection magnetic field, and the deflection magnetic field is configured to adjust the deflection angle of the electron beams passing between the oppositely arranged electromagnets.

Optionally, the deflection control assembly further includes a focusing magnet; and the focusing magnet is configured to focus the deflected electron beams, and the focused electron beams are made to impact the target material vertically.

Optionally, the X-rays passing through the collimating holes are a pencil-shaped X-ray beam at a megavolt level.

Optionally, a diameter of the pencil-shaped X-ray beam is less than 3 mm.

Optionally, the target includes one of a tumor target spot and a tumor target region.

In another aspect, a radiotherapy apparatus is provided. The radiotherapy apparatus includes a rotating gantry and the radiotherapy head as described in the above aspect.

The radiotherapy head is provided on the rotating gantry, and the rotating gantry can drive the radiotherapy head to rotate around a rotation axis of the rotating gantry.

Optionally, the collimator in the radiotherapy head includes at least one collimating hole set, each collimating hole set includes a plurality of collimating holes, and the radiotherapy head meets at least one of the following conditions:

the plurality of collimating holes in each collimation hole set are arranged along an extension direction of the rotation axis; and the radiotherapy head can move along the extension direction of the rotating axis.

Optionally, the deflection control assembly in the radiotherapy head is fixedly provided relative to the rotating gantry.

Optionally, the rotating gantry is one of a ring gantry and a C-arm gantry.

The technical solutions according to the present disclosure have the following beneficial effects.

By providing the target material at the entrance of each collimation hole, and the electron beams emitted by the electron accelerator impact the target material and the target material converts the electron beams into the X-rays, so that the X-rays can enter each collimating hole directly from the entrance of each collimating hole. Compared with the related art, the number of X-rays entering the collimating holes is greatly increased and thus the utilization rate of the X-rays is improved. In addition, since the deflection control assembly can be fixedly provided on the gantry which facilitates the control of the deflection control assembly for adjusting the deflection angle of the electron beams, the angle of the X-rays can be adjusted without depending on the mechanical deflection of the radiotherapy head, so that the focusing accuracy of the X-rays will not be limited by the mechanical movement accuracy of the radiotherapy head. As a result, the focusing accuracy of the X-rays on the target is effectively improved when the target is irradiated, and the implementation of non-coplanar irradiation is facilitated.

DETAILED DESCRIPTION

The embodiments of the present disclosure will be described in further detail with reference to the attached drawings to illustrate the objectives, technical solutions and advantages of the present disclosure more clearly.

In the related art, a radiotherapy head used in an X-ray knife technology generally includes: an electron accelerator, a flight tube, a target material, and a single-hole collimator, and the target material is provided at an exit of the flight tube. A radiotherapy process includes: electron beams emitted by the electron accelerator are transmitted in the flight tube and then irradiated on the target material, the target material then converts the electron beams into X-rays; and the single-hole collimator shapes the X-rays entering the interior of the single-hole collimator; and the shaped X-rays irradiate a tumor focus region, thereby killing tumor cells in the tumor focus region.

However, after the electron beams emitted by the electron accelerator are irradiated to the target material, the target material converts the electron beams into the X-rays that are divergently emitted, leading to a divergent area considerably greater than an area of the entrance of the single-hole collimator when the X-rays reach the single-hole collimator. As a result, the utilization rate of the X-rays in the related art is low.

Figure 1:
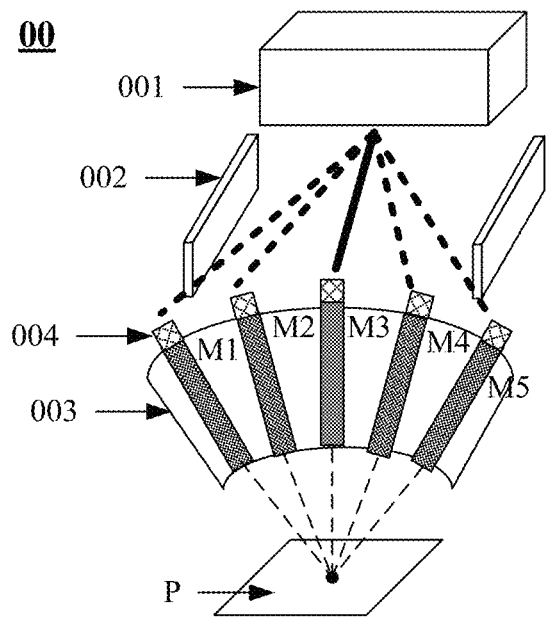
FIG. 1 illustrates a schematic structural diagram of a radiotherapy head according to an embodiment of the present disclosure.

FIG. 1 is a schematic structural diagram of a radiotherapy head according to an embodiment of the present disclosure. As shown in FIG. 1, the radiotherapy head 00 includes: an electron accelerator 001, a deflection control assembly 002, a collimator 003, and a target material 004. The deflection control assembly 002 is provided between the electron accelerator 001 and the collimator 003; the collimator is provided with a collimating hole; and the target material 004 is provided at an entrance of the collimating hole.

The deflection control assembly 002 is configured to adjust a deflection angle of electron beams emitted by the electron accelerator 001, and emit the angle-deflected electron beams to the target material 004.

The target material 004 is configured to convert the electron beams emitted to the target material 004 into X-rays.

As an example, the target material may be a material such as gold or tungsten.

The collimator 003 is configured to project the X-rays to a target via the collimating hole.

Said target is a tumor focus target. For example, the target may be a tumor target spot or a tumor target region of a patient.

In summary, in the radiotherapy head according to the embodiments of the present disclosure, the target material is provided at the entrance of the collimation hole, and the electron beams emitted by the electron accelerator impact the target material which then converts the electron beams into the X-rays, so that the X-rays can enter the collimating hole directly from the entrance of the collimating hole. Compared with the related art, the present disclosure greatly increases the number of X-rays entering the collimating holes, thereby improving the utilization rate of the X-rays.

Optionally, the collimator 003 may include at least one collimating hole set. For example, as shown in FIG. 1, the collimator 003 may include 5 collimating hole sets (M1 to M5), each of which includes a plurality of collimating holes. Accordingly, a piece of target material may be provided correspondingly at the entrance of each collimating hole. For example, if each collimating hole set includes 5 collimating holes, each collimating hole set is then correspondingly provided with 5 pieces of target materials. Moreover, the deflection control assembly 002 is configured to adjust the deflection angle of the electron beams emitted by the electron accelerator 001 so that the electron beams sequentially impact the target materials at the entrances of the plurality of collimating holes in a target collimating hole set. The target collimating hole set is one of the at least one collimating hole set. In this way, the target may be subject to focused irradiation with the collimator having a plurality of collimating holes by adjusting the deflection angle of the electron beams.

Optionally, the collimator according to the embodiment of the present disclosure may be an arc-shaped focusing collimator. Of course, the collimator for focused irradiation may also be rectangular parallelepiped and the like, and the shape of the collimator is not limited in the embodiments of the present disclosure.

Figure 2:
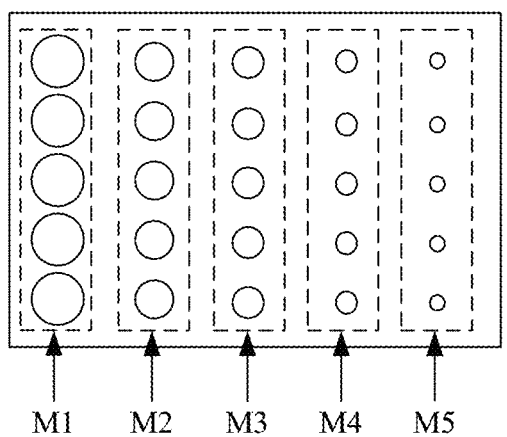
FIG. 2 illustrates a schematic structural diagram of a collimator according to an embodiment of the present disclosure.

Optionally, the collimator according to an embodiment of the present disclosure includes a plurality of collimating hole sets; the collimating holes in each collimating hole set are same in aperture; and the bore diameters of collimating holes in different collimating hole sets are different. As an example, FIG. 2 is a schematic structural diagram of a collimator according to an embodiment of the present disclosure. As shown in FIG. 2, the collimator includes 5 collimating hole sets (M1 to M5); the bore diameters of collimating holes in each collimating hole set are same; and the bore diameters of collimating holes in different collimating hole sets of the 5 collimating hole sets are different. It should be noted that the irradiation treatment for targets of different sizes can be implemented by setting a plurality of collimating hole sets and the bore diameters of collimating holes in different collimating hole sets are different. For example, a collimating hole set with a small bore diameter may be selected for precise irradiation treatment of small tumors, and a collimating hole set with a large bore diameter may be selected for irradiation treatment of large tumors.

The selected collimating hole set may be determined according to actual needs, which is not limited in the embodiments of the present disclosure.

Optionally, the bore diameters of the collimating holes in each collimating hole set of the collimator may include at least one of 5 mm, 8 mm, 15 mm, 20 mm and 35 mm.

Optionally, the deflection angle of the electron beams is in one-to-one correspondence to the positions of the plurality of collimating holes. A process of adjusting the deflection angle of the electron beams by the deflection control assembly 002 may include: the deflection control assembly 002 receives a target deflection angle, and then adjusts the deflection angle of the electron beams emitted by the electron accelerator 001 to the target deflection angle. Moreover, the target deflection angle is an angle to which the deflection angle of the electron beams needs to be adjusted, and the target deflection angle is one of a plurality of adjustable deflection angles to which the deflection control assembly 002 can deflect the electron beams.

Optionally, the deflection control assembly 002 may include a signal receiving element, a current loading element, and oppositely arranged electromagnets. After the signal receiving element receives the target deflection angle, the current loading element may load the electromagnets with a corresponding magnitude of current according to the target deflection angle. The oppositely arranged electromagnets are configured to form a deflection magnetic field, so as to adjust the deflection angle of the electron beams passing between the oppositely arranged electromagnets through the deflection magnetic field, and thus the deflection angle of the electron beams is adjusted to the target deflection angle under the action of the deflection magnetic field.

Optionally, according to the characteristics of different tumors, the deflection control assembly may control the deflection angle of the electron beams so that the electron beams sequentially impact the target materials at the entrances of the plurality of collimating holes in the target collimating hole set on the basis of a certain time distribution. For example, the electron beams may be allowed to impact each collimating hole in the target collimating holes set at the same time, so that the time of irradiation treatment for the target at different non-coplanar angles is the same, thereby reducing the damage to normal tissues.

Optionally, the deflection control assembly further includes: a focusing magnet. The focusing magnet is configured to focus the deflected electron beams so that the focused electron beams impact the target material vertically. Because the electron beams emitted by the electron accelerator have high energy in the middle and low energy at the periphery, a focusing magnet is provided at a position close to the collimator in the deflection control assembly. The focusing magnet may include at least one electrified solenoid. By virtue of the characteristic that a magnetic field outside the electrified solenoid is strong at both ends and weak in the middle, the electron beams are converged towards the central region of the target material and then deflected to be vertical to an incident surface of the target material, and thus become non-divergent electron beams, thereby ensuring that the energy of the electron beams used to impact the target material at the entrance of each collimating hole is the same. As a result, the energy of the X-rays emitted from each collimating hole to the target is the same, a radiation dose to normal tissues and organs around the target is homogenized, and damages to the normal tissues are reduced.

It should be noted that, by deflecting and focusing the electron beams through the deflection control assembly, the electron beams may be focused into an electronic pencil beam with a diameter less than 3 mm. The electronic pencil beam impacts the corresponding target material, which then converts the electronic pencil beam into the X-rays; the X-rays passing through the collimating holes in the collimator may be shaped into a pencil-shaped X-ray beam, that is, the X-rays passing through the collimator are a megavolt-level pencil-shaped X-ray beam, which has a focal spot with a diameter ranging from 3 mm to 5 mm.

Optionally, the electron accelerator may include at least one of a linear accelerator (also referred to as a linear resonance accelerator) and a cyclotron (also referred to as a cyclotron resonance accelerator). Moreover, the electron accelerator includes an accelerating tube, which is configured to accelerate the electron beams entering the accelerator tube. Moreover, the accelerating tube may be a traveling-wave accelerating tube or a standing-wave accelerating tube.

Optionally, the energy of an electron beam generated by the electron accelerator is 2-8 meV. The average energy of the X-rays is 0.6-3 MeV. The electron beam generated by the electron accelerator may generate megavolt-level X-rays, the energy of which is higher than that of the X-rays generated by the radiation source used in the gamma knife technology. This is more beneficial for the treatment of tumors at deep sites. Also, when a radiation dose required for treating a tumor is a constant value, the high-dose X-rays may shorten the time for treating the tumor, and reduce the instability caused by organ movement during the treatment. In addition, the high-dose X-rays provide a possibility for increasing a space for treatment, creating a large bore diameter for treatment and achieving a larger non-coplanar rotation angle.

In summary, in the radiotherapy head according to the embodiments of the present disclosure, the target material is provided at the entrance of each collimation hole, and the electron beams emitted by the electron accelerator impact the target material which then converts the electron beams into the X-rays, so that the X-rays can enter each collimating hole directly from the entrance of each collimating hole. Compared with the related art, the present disclosure greatly increases the number of X-rays entering the collimating holes, thereby improving the utilization rate of the X-rays.

Figure 3:
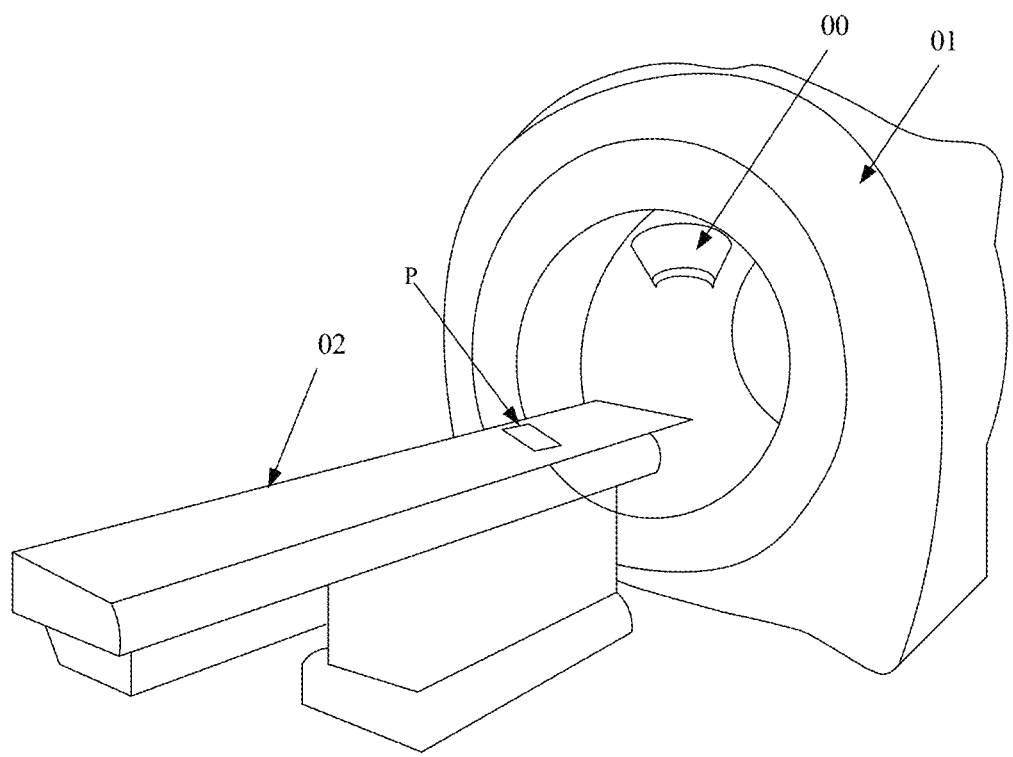
FIG. 3 illustrates a schematic structural diagram of a radiotherapy apparatus according to an embodiment of the present disclosure.

FIG. 3 is a schematic structural diagram of a radiotherapy apparatus according to an embodiment of the present disclosure. As shown in FIG. 3, the radiotherapy apparatus includes: a rotating gantry 01 and a radiotherapy head 00 as shown in FIG. 1. The radiotherapy head 00 is provided on the rotating gantry 01, and the rotating gantry 01 may drive the radiotherapy head 00 to rotate around a rotation axis of the rotating gantry 01.

Optionally, referring to FIG. 3, the rotating gantry 01 has a central opening for accommodating a treatment couch 02, which extends in a direction in parallel to the direction in which the rotation axis of the rotating gantry 01 is located.

Optionally, the rotating gantry 01 may be a ring gantry, for example, a high-precision ring gantry with a rotation isocentric accuracy of less than 0.5 mm may be selected; or the rotating gantry 01 may also be a C-arm gantry. The type of the rotating gantry is not limited in the embodiments of the present disclosure.

Optionally, the collimator in the radiotherapy head 00 includes at least one collimating hole set, each of which includes a plurality of collimating holes. The radiotherapy head 00 meets at least one of the following conditions: the plurality of collimating holes in each collimating hole set are arranged along an extension direction of the rotation axis of the rotating gantry; and the radiotherapy head may move along the extension direction of the rotation axis. That is, the radiotherapy head 00 meets the following condition: the plurality of collimating holes in each collimating hole set are arranged along the extension direction of the rotation axis of the rotating gantry; or the radiotherapy head may move along the extension direction of the rotation axis; or, the plurality of collimating holes in each collimating hole set are arranged along the extension direction of the rotation axis of the rotating gantry and the radiotherapy head may move along the extension direction of the rotation axis.

As an example, referring to FIGS. 1 and 3, the plurality of collimating hole sets are arranged in an array along the direction of the rotation axis of the rotating gantry, and the plurality of collimating holes in each collimating hole set are arranged along the extension direction of the rotation axis of the rotating gantry. Moreover, as shown in FIG. 1, a line of geometric centers of the exits of the plurality of collimating holes in each collimating hole set may have an arc shape, the center of the arc shape coincides with the center of a target P, i.e., coinciding with a point of intersection of the X-rays.

It should be noted that since the plurality of collimating holes in each collimating hole set are arranged along the extension direction of the rotation axis of the rotating gantry, the non-coplanar irradiation of the target may be implemented when the rotating gantry rotates, thereby reducing the damage to the normal tissues. In the embodiment of the present disclosure, during the irradiation of the target, the non-coplanar irradiation treatment of the target can be realized without moving the treatment couch, thereby guaranteeing the treatment accuracy. In addition, the use of the focused collimator can increase the sharpness of the edge of an irradiation field, and the irradiation field refers to a region irradiated by the X-rays.

Optionally, the radiotherapy head may move along the extension direction of the rotating axis. Moreover, the radiotherapy head may be provided on an arc-shaped guide rail that is provided along the extension direction of the rotation axis of the rotating gantry, and a center of the arc-shaped guide rail coincides with the center of the target. When the radiotherapy head moves along the extension direction of the arc-shaped guide rail, the non-coplanar irradiation of the target can be implemented in a plurality of directions without moving the treatment couch, thereby reducing the damage to the normal tissues.

Optionally, the deflection control assembly in the radiotherapy head is fixedly provided relative to the rotating gantry.

As an example, a working process of the radiotherapy apparatus shown in FIG. 3 may be as follows.

Before performing the irradiation treatment on the target, the target collimating hole set having a corresponding bore diameter is selected according to the size of the target P on the treatment couch 02; the deflection angles in one-to-one correspondence to the collimating holes are determined according to a positional relationship between the plurality of collimating holes and the electron accelerator and a corresponding relationship between the positions of the collimating holes and the deflection angles is established; and the position of the treatment couch is adjusted according to the position of the target. During the irradiation treatment of the target, the electron accelerator generates electron beams; the deflection angle of the electron beams is adjusted by the deflection control assembly according to the corresponding relationship between the positions of the collimating holes and the deflection angles, so that the electron beam sequentially impacts the target materials at the entrances of the plurality of collimating holes according to a time sequence relationship; the collimating holes in the collimating hole set are arranged along the extension direction of the rotation axis of the rotating gantry, the radiotherapy head 00 is driven by autorotation of the rotating gantry 01 to rotate around the rotation axis with the rotational axis as a center, and the radiotherapy head 00 is controlled to move along the arc-shaped guide rail, thereby enabling the irradiation treatment of the tumor at a plurality of non-coplanar angles.

It can be seen from the working process of the radiotherapy apparatus that, during the irradiation treatment of the tumor, the collimating holes in the collimating hole set are arranged along the extension direction of the rotation axis of the rotating gantry, and/or when the radiotherapy head is controlled to move on the arc-shaped guide rail that is provided along the direction of the rotation axis, the radiation treatment of the tumor at different non-coplanar angles can be implemented when the rotating gantry rotates, thereby reducing the damage to the normal tissues.

Optionally, the radiotherapy apparatus may further include a plurality of rows of ionization chambers, which may be provided below the collimator for real-time monitoring of the intensity of the X-rays.

The radiotherapy apparatus according to the embodiments of the present disclosure may also be used simultaneously with other X-ray accelerators that can be installed on the rotating gantry, in order to meet diverse treatment needs.

It should be noted that, in the embodiments of the present disclosure, the non-coplanar angle refers to an included angle between the X-rays emitted from the collimator and a rotation plane of the rotating gantry.

In summary, in the radiotherapy apparatus according to the embodiments of the present disclosure, the target material is provided at the entrance of each collimation hole, and the electron beams emitted by the electron accelerator impact the target material and the target material converts the electron beams into the X-rays, so that the X-rays can enter each collimating hole directly from the entrance of each collimating hole. Compared with the related art, the number of the X-rays entering the collimating holes is greatly increased, and thus the utilization rate of the X-rays is improved. In addition, since the deflection control assembly is fixedly provided on the rotating gantry which facilitates the control of the deflection control assembly for adjusting the deflection angle of the electron beams, the angle of the X-rays can be adjusted without depending on the mechanical deflection of the radiotherapy head, so that the focusing accuracy of the X-rays will not be limited by the mechanical movement accuracy of the radiotherapy head. As a result, the focusing accuracy of the X-rays on the target is effectively improved when the target is irradiated, and the implementation of non-coplanar irradiation is facilitated. Further, based on the rotation of the radiotherapy head along the rotation axis, the plurality of collimating holes in each collimating hole set are arranged along the extension direction of the rotation axis, and/or, the radiotherapy head is controlled to move axially along the arc-shaped guide rail. Therefore, a larger non-coplanar angle can be achieved without moving the treatment couch and the damage to the normal tissues is reduced.

The term "and/or" in the present disclosure is merely to describe an association relationship between associated objects, indicating that there may be three types of relationships. For example, A and/or B may indicates three types of relationships, namely, A exists alone, or both A and B exist, or B exists alone. In addition, the character "/" herein generally indicates that there is an "or" relationship between associated front and back objects.

Described above are merely optional embodiments of the present disclosure, which are not intended to limit the present disclosure. Any modifications, equivalent substitutions, improvements and the like made within the spirit and principle of the present disclosure shall fall within the protection scope of the present disclosure.

The invention claimed is:

1. A radiotherapy apparatus, comprising:
a rotating gantry and a radiotherapy head,
wherein the radiotherapy head is provided on the rotating gantry, and the rotating gantry can drive the radiotherapy head to rotate around a rotation axis of the rotating gantry, and the radiotherapy head comprises: an electron accelerator, a deflection control assembly, a collimator, and a target material,
wherein the deflection control assembly is provided between the electron accelerator and the collimator, the collimator is provided with a plurality of collimating holes, and the target material is provided at an entrance of each of the plurality of collimating holes,
wherein the deflection control assembly is configured to adjust a deflection angle of an electron beam emitted by the electron accelerator, and emit the electron beam to the target material,
wherein the target material is configured to convert the electron beam emitted to the target material into X-rays, and
wherein the collimator is configured to project the X-rays to a target via the plurality of collimating holes.

2. The radiotherapy apparatus according to claim 1, wherein the plurality of collimating holes of the collimator in the radiotherapy head is divided into at least two collimating hole sets, each collimating hole set comprises a plurality of collimating holes having the same bore diameter, any two collimating holes in different collimating hole sets have different bore diameters, and the radiotherapy head meets at least one of the following conditions:
the plurality of collimating holes in each collimating hole set are arranged along an extension direction of the rotation axis; and
the radiotherapy head can move along the extension direction of the rotating axis.

3. The radiotherapy apparatus according to claim 1, wherein the deflection control assembly in the radiotherapy head is fixedly provided on the rotating gantry.

4. The radiotherapy apparatus according to claim 1, wherein the rotating gantry is one of a ring gantry and a C-arm gantry.

5. The radiotherapy apparatus according to claim 2, wherein the deflection control assembly is configured to adjust the deflection angle of the electron beam emitted by the electron accelerator so that the electron beam sequentially impact corresponding parts of the target material at entrances of collimating holes in a target collimating hole set, wherein the target collimating hole set is one of the at least two collimating hole sets.

6. The radiotherapy apparatus according to claim 2, wherein bore diameters of collimating holes in the at least two collimating hole sets comprise at least one of 5 mm, 8 mm, 15 mm, 20 mm or 35 mm.

7. The radiotherapy apparatus according to claim 2, wherein the collimator is an arc-shaped focusing collimator.

8. The radiotherapy apparatus according to claim 1, wherein the deflection control assembly comprises oppositely arranged electromagnets; and
the oppositely arranged electromagnets are configured to form a deflection magnetic field, and the deflection magnetic field is configured to adjust the deflection angle of the electron beams passing between the oppositely arranged electromagnets.

9. The radiotherapy apparatus according to claim 8, wherein the deflection control assembly further comprises a focusing magnet; and
the focusing magnet is configured to focus deflected electron beams, and focused electron beams are made to impact the target material vertically.

10. The radiotherapy apparatus according to claim 1, wherein the X-rays passing through the collimating hole are a pencil-shaped X-ray beam at a megavolt level.

11. The radiotherapy apparatus according to claim 10, wherein a diameter of the pencil-shaped X-ray beam is less than 3 mm.

12. The radiotherapy apparatus according to claim 1, wherein the target comprises one of a tumor target spot and a tumor target region.

* * * * *